(12) United States Patent
Lim et al.

(10) Patent No.: US 10,888,688 B2
(45) Date of Patent: *Jan. 12, 2021

(54) MICROINJECTION CATHETER

(71) Applicant: The Regents of the University of California, UCSF, Oakland, CA (US)

(72) Inventors: Daniel A. Lim, San Francisco, CA (US); Matthew Silvestrini, San Francisco, CA (US); Tejal Desai, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/148,935

(22) Filed: Oct. 1, 2018

(65) Prior Publication Data

US 2019/0030281 A1    Jan. 31, 2019

Related U.S. Application Data

(62) Division of application No. 14/417,460, filed as application No. PCT/US2013/052301 on Jul. 26, 2013, now Pat. No. 10,099,034.

(Continued)

(51) Int. Cl.
*A61M 25/00*    (2006.01)
*A61M 25/06*    (2006.01)
(Continued)

(52) U.S. Cl.
CPC ...... *A61M 25/007* (2013.01); *A61M 25/0662* (2013.01); *A61B 18/1492* (2013.01);
(Continued)

(58) Field of Classification Search
CPC ...... A61M 2025/0681; A61M 25/0662; A61M 2025/0004; A61M 2025/018
See application file for complete search history.

(56) References Cited

U.S. PATENT DOCUMENTS 6,190,353 B1    2/2001    Makower et al.
8,192,403 B1    6/2012    Pursley
(Continued)

OTHER PUBLICATIONS

International Search Report and Written Opinion of PCT/US2013/052301 dated Oct. 24, 2013, 21 pages.

*Primary Examiner* — Emily L Schmidt
(74) *Attorney, Agent, or Firm* — Mintz, Levin, Cohn, Ferris, Glovsky and Popeo, P.C; Pedro Suarez; Paul Brockland

(57) ABSTRACT

An insertion device for delivering media inside a patient includes an outer guide tube having a side port. An inner guide tube is nested within the outer guide tube and movable axially within the outer guide tube. The inner guide tube includes a deflector at an end within the outer guide tube. The device also includes a catheter nested within the inner guide tube and movable axially within the inner guide tube. The deflector of the inner guide tube is positionable such that it deflects the dispensing end of the catheter outward through the opening in the outer guide tube when the catheter is advanced axially within the inner guide tube. A therapeutic delivery cannula may be nested within the catheter, such that the deflected end of the catheter determines the direction of travel of the therapeutic delivery cannula into patient tissue when the cannula emerges from the catheter.

5 Claims, 12 Drawing Sheets

Related U.S. Application Data

(60) Provisional application No. 61/676,767, filed on Jul. 27, 2012.

(51) Int. Cl.
*A61M 25/01* (2006.01)
*A61B 18/14* (2006.01)

(52) U.S. Cl.
CPC . *A61M 25/0041* (2013.01); *A61M 2025/0004* (2013.01); *A61M 2025/018* (2013.01); *A61M 2025/0175* (2013.01); *A61M 2025/0681* (2013.01); *A61M 2210/0693* (2013.01)

(56) References Cited

U.S. PATENT DOCUMENTS

| | | |
|---|---|---|
| 10,099,034 B2 | 10/2018 | Lim et al. |
| 2002/0002349 A1 | 1/2002 | Flaherty et al. |
| 2002/0103459 A1* | 8/2002 | Sparks ............... A61B 17/3207 |
| | | 604/164.13 |
| 2002/0123698 A1 | 9/2002 | Garibotto et al. |
| 2008/0058759 A1 | 3/2008 | Makower et al. |
| 2009/0198213 A1 | 8/2009 | Tanaka |
| 2009/0198218 A1 | 8/2009 | Gill et al. |
| 2010/0016836 A1 | 1/2010 | Makower et al. |
| 2010/0145371 A1 | 6/2010 | Rosenbluth et al. |
| 2010/0222744 A1 | 9/2010 | Riek et al. |
| 2011/0282319 A1 | 11/2011 | Gill et al. |

* cited by examiner

DEPLOYED　　DEPLOYED　　RETRACTED　　CLOSED

MICROINJECTION CATHETER

CROSS REFERENCE TO RELATED APPLICATIONS

This application is a divisional application of U.S. application Ser. No. 14/417,460 filed on Jul. 26, 2013 and titled "Microinjection Catheter" which claims priority to U.S. Provisional Patent Application No. 61/676,767 filed Jul. 27, 2012 and titled "Microinjection Catheter", and to International Patent Application No. PCT/US2013/052301 filed Jul. 26, 2013 also titled "Microinjection Catheter, the entire disclosure disclosures of which are hereby incorporated by reference for all purposes.

BACKGROUND OF THE INVENTION

Cell therapy has shown great promise in the treatment of a wide range of neurological diseases, including Parkinson's disease (PD), Huntington's disease, and stroke.

To date, cell therapies have been delivered to the human brain with a stereotactically inserted straight cannula. While effective for small animal experimental models, straight cannula transplantation strategies present significant challenges when scaled-up for human therapy. The human brain is 800 to 2300 times larger than that of rodents used for preclinical research. With a straight cannula, cell delivery to the larger target volumes of human brain requires several independent brain penetrations. Some patients with PD have received up to 16 separate penetrations for transplantation to the putamen. Every transcortical brain penetration injures normal brain tissue and threatens hemorrhagic stroke.

In one approach to translational scale-up, very large numbers of cells can be delivered to a single location or along a short segment of the cannula tract. Unfortunately, the implantation of a large mass of cells within a confined location can severely impair graft viability, resulting in necrosis at the center of the transplant.

Another approach has been to insert a large host catheter, which is comprised of a number of internal passages, or lumens for the advancement of micro-catheters. These internal passages within the host catheter exit at specified distal orifice locations around the distal end to allow the delivery of a media to a desired target area. Using this approach, the host catheter is inserted into the center of the desired target, or delivery area in the patient. Then, the micro-catheters are inserted into the various lumens, where multiple doses can be delivered to each of the distal orifice locations along the elongate member. This method allows a larger target area to be covered without the need for multiple cranial penetrations. The introduction of a relatively large host catheter displaces a larger amount of tissue and the use of multiple micro catheters makes the ability to deliver a metered injection more difficult due to their variable lengths.

A problem with at least some prior systems is that the delivered media may not stay at the desired delivery site. In a phenomenon called reflux, a portion of the media may flow back up the penetration shaft, significantly reducing the amount of media that remains at the treatment site. Larger injection volumes worsen the reflux of infused materials along the penetration tract making cell dosing unpredictable in terms of numbers as well as final graft location.

In most clinical trials, a syringe is used to deliver cells through the inserted cannula. Unless the syringe is kept in constant motion, the cells naturally sediment to the most dependent location, usually the end attached to cannula. Thus, the first partial injection volume from a syringe may contain far more cells than those dispensed later, further contributing to unpredictable variability of cell dosing. The use of a syringe having a larger diameter than the catheter main lumen may make it difficult to control the volume of each dose, and may subject the cells to shear and other mechanical forces that result in the decrease of cell viability for cell transplantation.

BRIEF SUMMARY OF THE INVENTION

An insertion device for delivering media inside a patient includes an outer guide tube having a closed end configured for insertion into patient tissue. The outer guide tube defines a side port in a wall of the guide tube near the closed end. The insertion device also includes an inner guide tube nested within the outer guide tube and movable axially within the outer guide tube. The inner guide tube includes a deflector at an end within the outer guide tube. The device also includes a catheter nested within the inner guide tube and movable axially within the inner guide tube. The catheter has a dispensing end that defines one more dispensing holes for dispensing the media. The deflector of the inner guide tube is positionable in relation to the opening of the outer guide tube such that it deflects the dispensing end of the catheter outward through the opening in the outer guide tube when the catheter is advanced axially within the inner guide tube.

DETAILED DESCRIPTION OF THE INVENTION

Figure 1:
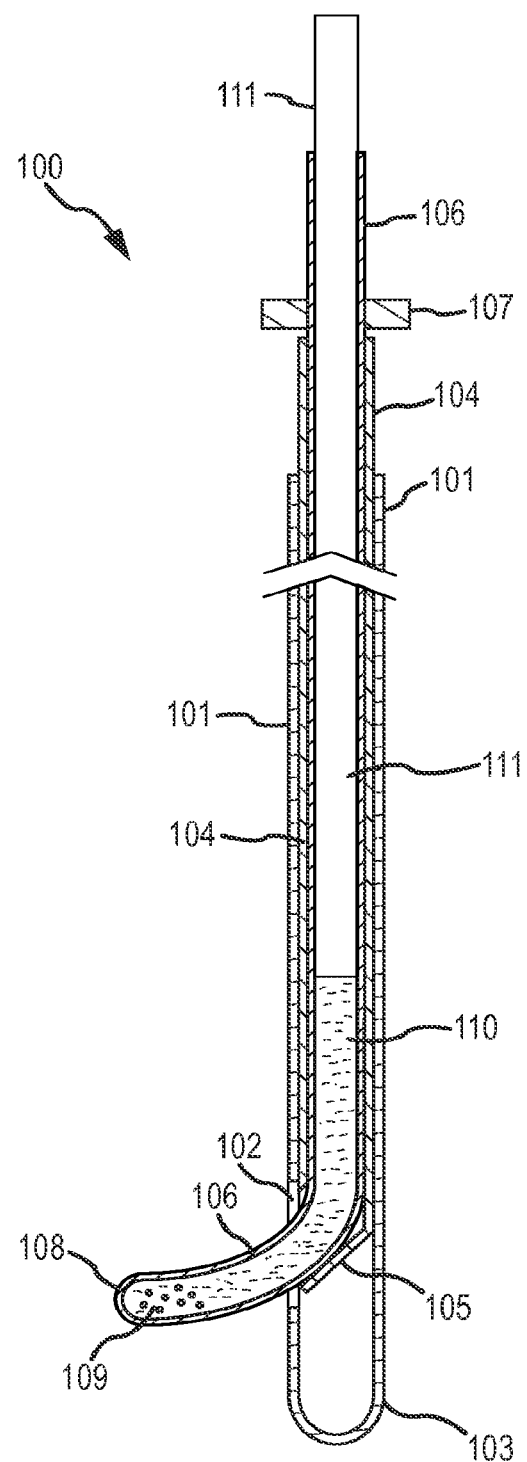
FIG. 1 illustrates an insertion device in accordance with an embodiment of the invention.

FIG. 1 illustrates an insertion device 100 in accordance with an embodiment of the invention. Example insertion device 100 includes a set of three tubes that assemble in a nested manner. An outer guide tube 101 may be rigid or semi-rigid, and may be made for example of stainless steel, polyetheretherketone (PEEK), or another suitable material. It should be noted that FIG. 1 is not necessarily to scale. The diameters of the components are exaggerated for clarity of illustration. Outer guide tube 101 may have an outer diameter suitable for the intended use of insertion device 100. In one example embodiment intended for placement of media into the human brain, outer guide tube 101 has an outer diameter of about 2.4 mm and an inner diameter of about 1.8 mm, although it is to be understood that other sizes may be used for treatment of the human brain, and may be especially helpful in the treatment of other human organs, or in the treatment of animals which may be larger or smaller than humans. In another example embodiment, outer guide tube 101 has an outer diameter of about 2.11 mm, an inner diameter of about 1.6 mm, and a length of about 38 cm or more.

Outer guide tube 101 includes a side port 102 placed a distance from distal end 103 of outer guide tube 101. In one example embodiment, side port 102 is placed about 4 mm from closed distal end 103, but other suitable dimensions may be used.

An inner guide tube 104 nests within outer guide tube 101. Inner guide tube 104 may also be rigid or semi-rigid, and may be made for example of stainless steel, nylon-12, or another suitable material. In one example embodiment, inner guide tube 104 has an outer diameter of about 1.65 mm and an inner diameter of about 1.19 mm, although other suitable dimension may be used. In another example embodiment, inner guide tube 104 has an outer diameter of about 1.47 mm, an inner diameter of about 1.07 mm, and a length of about 43 cm or more. Inner guide tube 104 is movable at least axially within outer guide tube 101, so that inner guide tube can cover or uncover (close or open) side port 102. Inner guide tube 104 may be lockable in the open and closed positions with respect to outer guide tube 101, for example using a Tuohy Borst adapter or other device (not shown). Inner guide tube 104 also includes a deflector 105, the purpose of which is explained in more detail below.

A flexible delivery catheter 106 translates within inner guide tube 104. Catheter 106 may be made, for example, of nylon-12, nylon-11, or another suitable material. In one example embodiment, catheter 106 has an outer diameter of about 1.0 mm and an inner diameter of about 0.4 mm, but other suitable dimensions may be used. Catheter 106 may be lockable with respect to inner guide tube 104 for example using another Tuohy Borst adapter or other device (not shown). A depth stop 107 may be provided to prevent inadvertent deployment of catheter 106 beyond its intended range.

At an insertion end 108 of catheter 106, one or more dispensing holes are provided for dispensing media 110. Any suitable number and arrangement of dispensing holes may be used. In the vicinity of insertion end 108, catheter 106 is preferably pre-formed into a curved shape. A heat set or other procedure may be used to pre-form insertion end 108. For example, in one example embodiment having a catheter made of nylon-12, the catheter was heat set using a lab oven for approximately 15 minutes after the glass transition temperature (170° F.) was achieved. This process provided the necessary environment to shape the catheter to the desired specifications. The catheter was both straightened and bent at the insertion end. A metal rod mandrel was placed in the inner lumen of the catheter excluding the last 1.5 cm from the distal end. This distal portion was then fixated to the desired radius of curvature (0.5 cm). After the allotted time, the catheter was removed from the oven yielding a cell delivery catheter with various radii of curvatures near the distal end.

During use, inner guide tube 104 may be positioned to align deflector 105 with side port 102. The combination of deflector 105 and the preset bend in catheter 106 causes catheter 106 to emerge from outer guide tube 101 approximately perpendicularly. In other embodiments, different deflector shapes and different preset bends may be used to achieve other angles of emergence. The system may be configured for any suitable maximum deployment of catheter 106. In one example embodiment, catheter 106 can protrude from outer guide tube 101 by up to 2.0 cm. Deflector 105 may be an angled, radiused, or have another suitable shape to accomplish the deflection of catheter 106.

A plunger 111 fits within catheter 106. Plunger 111 may be made from any suitable material, for example a Ti6Al4V (Grade 5 Titanium) wire. In one example embodiment, plunger 111 has an outer diameter of 0.4 mm and a flattened end, but other suitable sizes and shapes may be used. For example, the end of plunger 111 may be rounded, tapered, pointed, or have any other workable shape. A close fit between the walls of the catheter and the plunger wire may provide a nearly gas-tight seal to allow both aspiration and dispensing of fluids. Dip coating of the distal end of the plunger wire may further enhance this seal. For safety, a torquer (not shown) at the catheter proximal end prevents inadvertent movement of the plunger wire. To allow translational movement of the plunger wire, the user must open this plunger lock. Preferably, catheter 106 can be fixed at any deployed distance by closing the catheter lock while still allowing the user to manipulate the plunger wire by opening the plunger lock. Thus, advancement of the plunger wire does not result in movement of the catheter.

Figure 2:
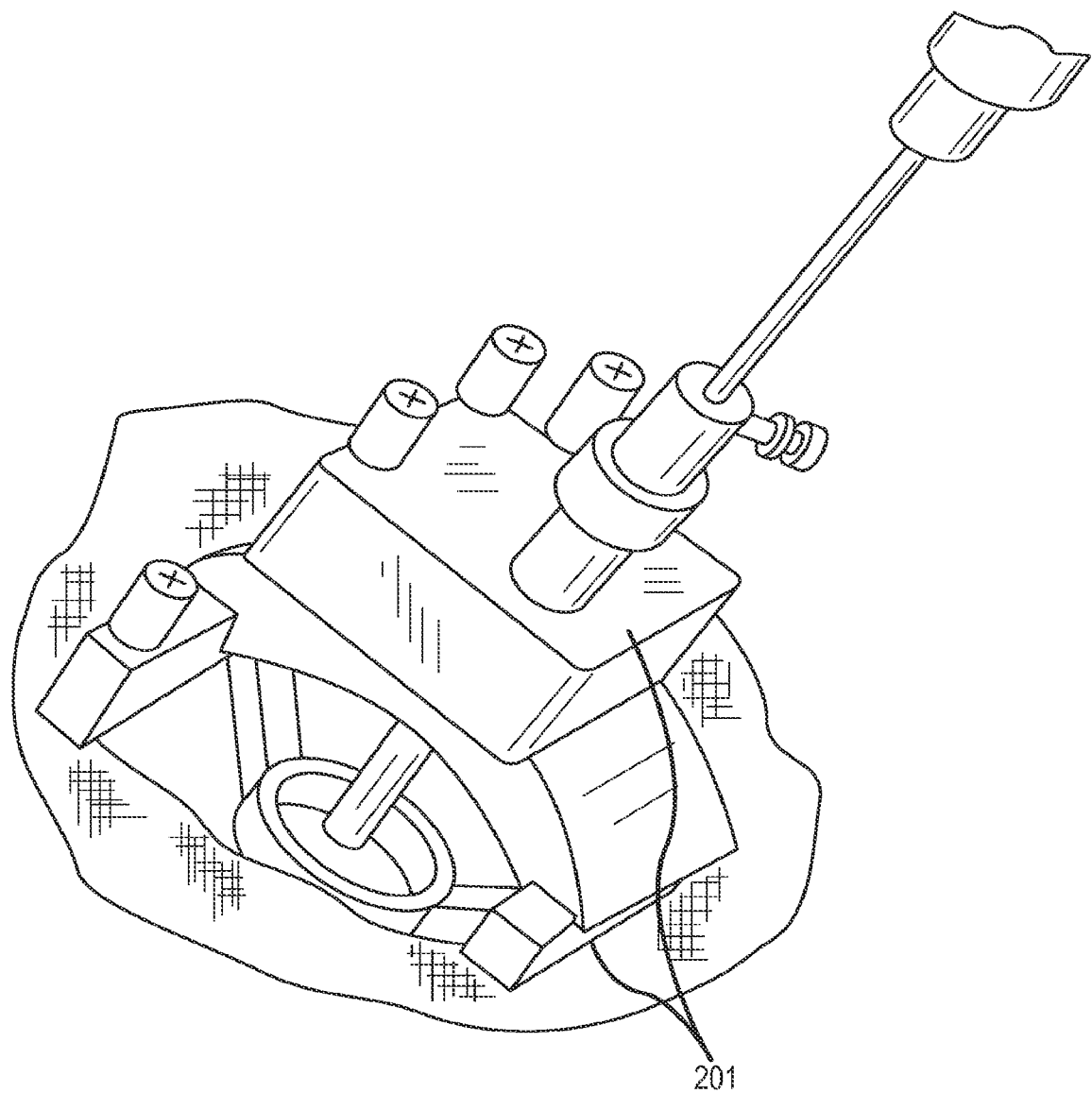
FIG. 2 shows an embodiment of the insertion device of FIG. 1 incorporated with a stereotactic frame for animal surgery.

To use insertion device 100, the user preferably plans an insertion trajectory into the tissue of the patient. Where feasible, the insertion may be planned and accomplished using stereotactic surgery techniques. For example, FIG. 2 shows an embodiment of insertion device 100 incorporated with a stereotactic frame 201 for animal surgery.

Whatever means are used to guide the insertion, at least outer guide tube 101 and inner guide tube 104 are inserted into the patient tissue to the desired insertion depth. Preferably, inner guide tube 104 is positioned so that side port 102 is closed during the insertion. Once the desired insertion depth is reached, the position of outer guide tube 101 may be locked. Catheter 106 and plunger 111 may be present within inner guide tube 104 during the insertion or may be inserted later.

Catheter 106 is loaded at any convenient time with media 110 to be dispensed to the patient tissue. For example media 110 may be a suspension of cells to be used for cell therapy. Side port 102 is opened by withdrawing inner guide tube 104, and inner guide tube 104 is preferably locked with respect to outer guide tube 101. Catheter 106 (along with plunger 111) is advanced so that insertion end 108 emerges through side port 102. When the desired protrusion distance is reached, catheter 106 is preferably locked in relation to inner guide tube 104. Plunger 111 may then be unlocked and advanced through inner guide tube 104 to force media 110 out through dispensing holes 109.

Once the desired dose has been delivered to the first treatment site, the process may be reversed to withdraw catheter 106 back into inner guide tube 104, and to close side port 102. Outer guide tube 101 may then be repositioned for delivery of media to a second treatment site. During the repositioning, outer guide tube 101 may be translated along its longitudinal axis (either advanced or retracted), rotated about its longitudinal axis, or moved in a combination of translation and rotation. When outer guide tube is in the desired position for dispensing media to a second treatment site, inner guide tube 104 is retracted to open side port 102, catheter 106 is advanced, and plunger 111 is advanced to dispense media 110 to the second treatment site.

This process may be repeated, so that a number of different treatment sites are accessed through a single original penetration of outer guide tube 101 into the patient tissue. In some embodiments, this process may be called radially branched deployment, and can result in delivery of media in a precise "tree-like" pattern within the patient tissue.

It will be recognized that variations on this basic procedure are possible. For example, while outer guide tube 101 is held in a single orientation, catheter 106 may be deployed to multiple distances with media 110 being dispensed at each of the multiple distances. In another variation, catheter 106 may be withdrawn and re-loaded with media 110, and re-inserted into inner guide tube 104 during the procedure. In another variation, catheter 106 may be replaced with a second pre-loaded catheter, so that some treatment sites receive media from a first catheter and some receive media from a second catheter, while still requiring only one penetration of patient tissue by outer guide tube 101.

This technique may be especially useful for complex treatment volumes. A variety of catheters may be provided having different preset bends, and different catheters may be used as needed to reach different parts of the treatment volume.

Figure 3:
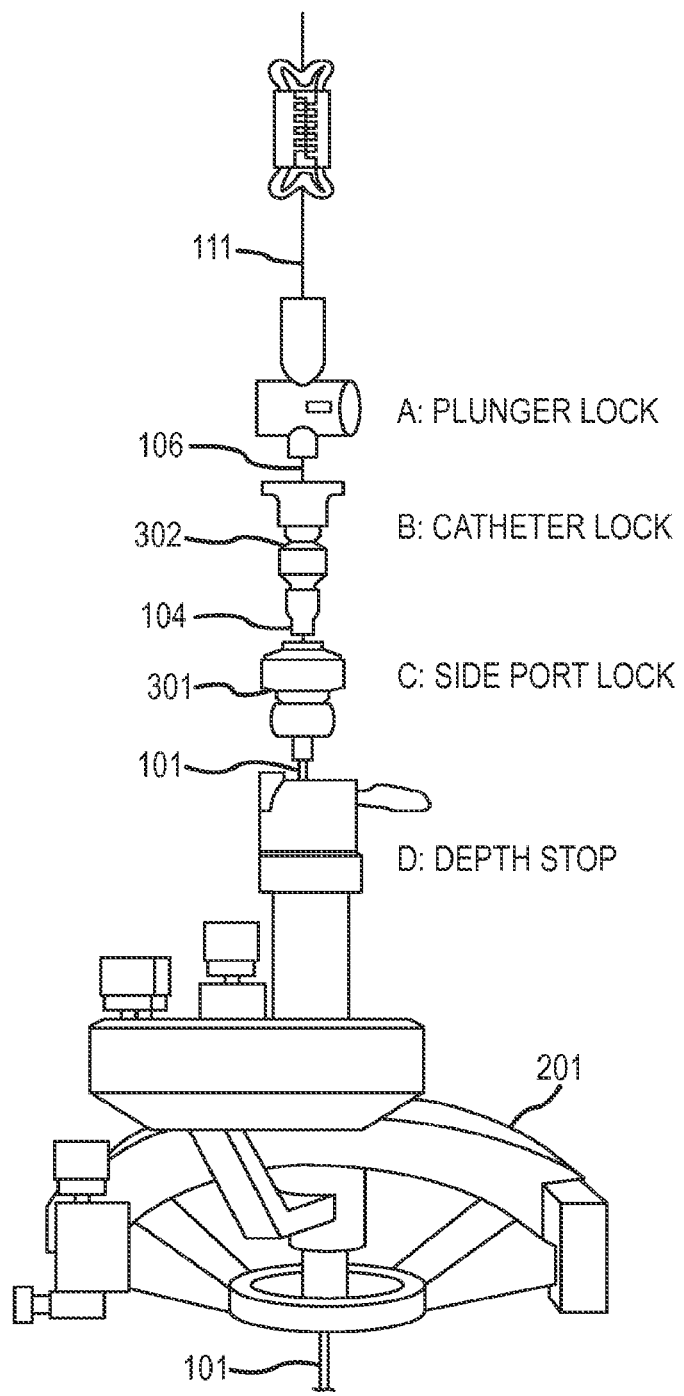
FIG. 3 illustrates additional components that may be used in accordance with embodiments.

FIG. 3 illustrates additional components that may be used in accordance with embodiments. In this example, a first Tuohy Borst adapter 301 is positioned to lock and unlock inner guide tube 104 in relation to outer guide tube 101, and a second Tuohy Borst adapter 302 is positioned to lock and unlock catheter 106 in relation to inner guide tube 104.

Figure 4:
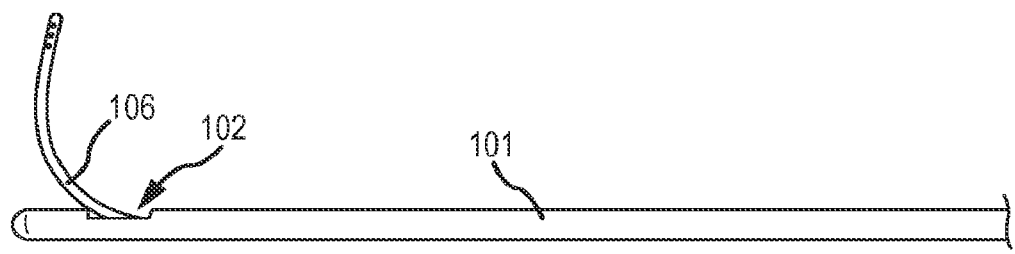
FIG. 4 illustrates the protrusion of a catheter from an outer guide tube through a side port, in an experimental embodiment.
Figure 5:
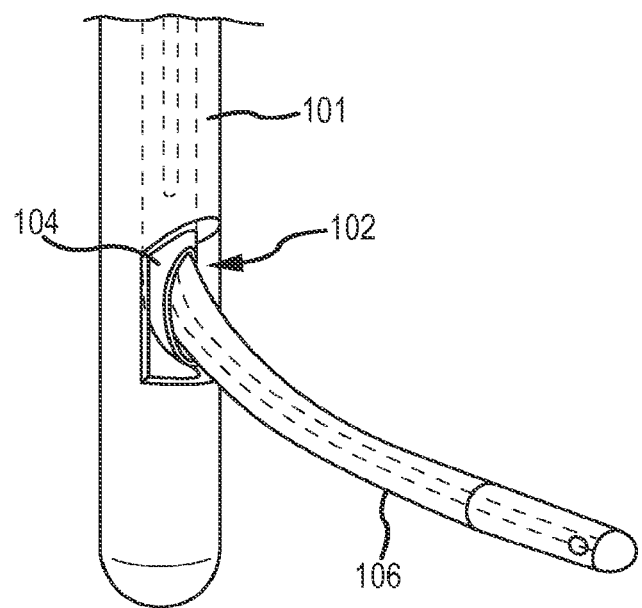
FIG. 5 also shows the protrusion of a catheter from an outer guide tube through a side port, in accordance with embodiments.

FIG. 4 illustrates the protrusion of catheter 106 from outer guide tube 101 through side port 102, in an experimental embodiment. FIG. 5 also shows the protrusion of catheter 106 from outer guide tube 101 through side port 102, in another view.

Figures 6A, 6B, 6C, 6D:
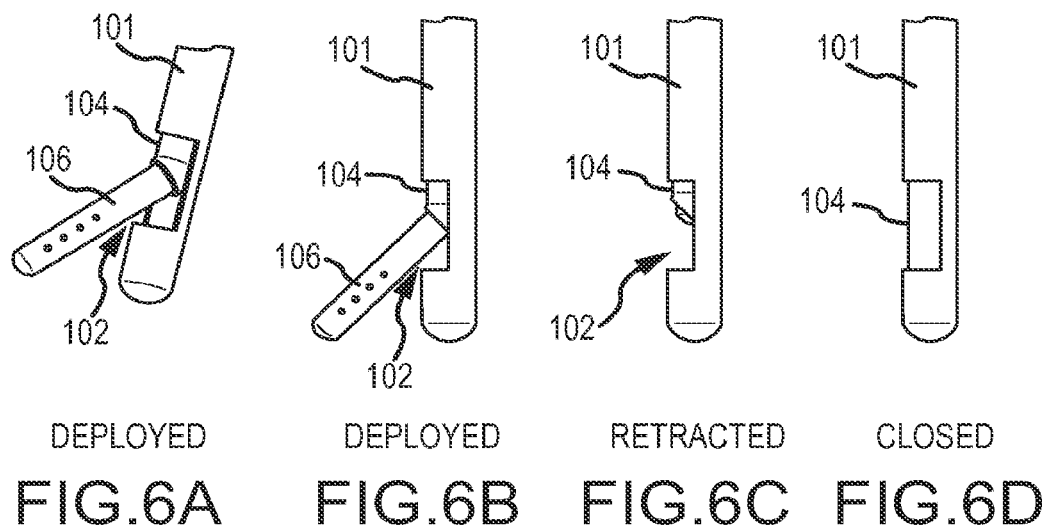
FIGS. 6A-6D illustrate the operation of the insertion device of FIG. 1 in more detail.

FIGS. 6A-6D illustrate the operation of insertion device 100 in more detail. A deployed position is shown in FIG. 6A and FIG. 6B, in which catheter 106 protrudes from outer guide tube 101 and inner guide tube 104 through side port 102. A retracted position is also shown in FIG. 6C, where side port 102 is open, but catheter 106 has been retracted within inner guide tube 104. Finally, FIG. 6D shows a closed position, where inner guide tube 104 has been advanced so that side port 102 is closed.

Figure 7:
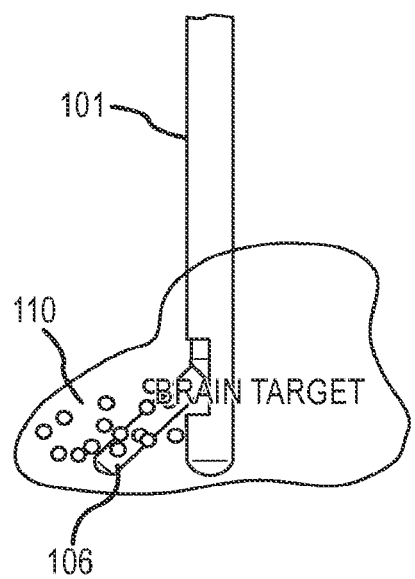
FIG. 7 illustrates the dispensing of media from a catheter into brain tissue, in accordance with embodiments.

FIG. 7 illustrates the dispensing of media 110 from catheter 106 into brain tissue, in accordance with embodiments.

Figure 8A:
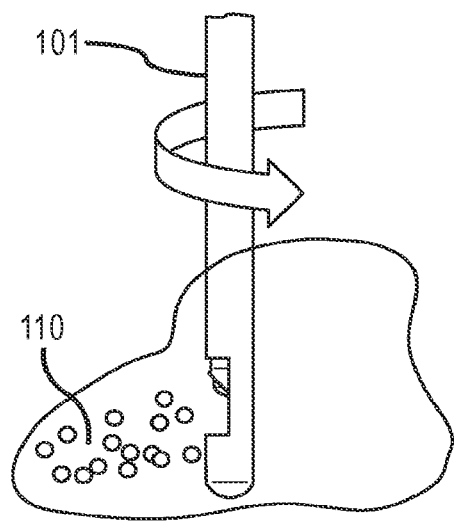
FIGS. 8A and 8B illustrate dispensing of media to a second treatment site, according to embodiments.
Figure 8B:
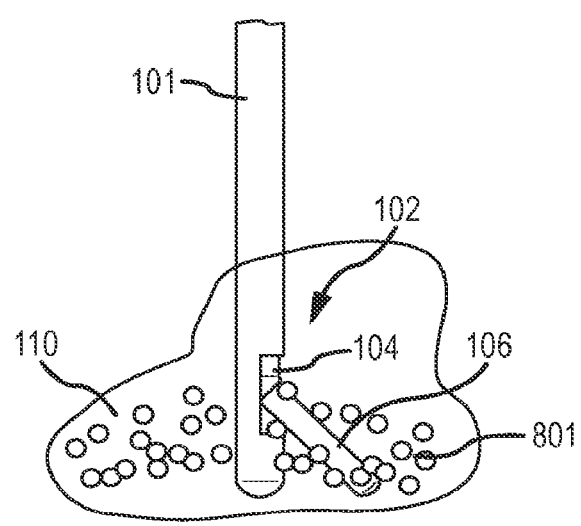

FIGS. 8A and 8B illustrate dispensing of media 110 to a second treatment site, according to embodiments. In FIG. 8A, catheter 106 has been retracted after dispensing media 110 to a first treatment site, and outer guide tube 101 is rotated. In some embodiments, inner guide tube 104 may also be advanced to close side port 102 during the rotation. In FIG. 8B, outer guide tube 101 has been rotated about its longitudinal axis, for dispensing a second dose of media 110 to a second treatment site. Inner guide tube 104 has been retracted to open side port 102, and catheter 106 has been extended, and additional media 801 is dispensed to a second treatment site.

Figure 9:
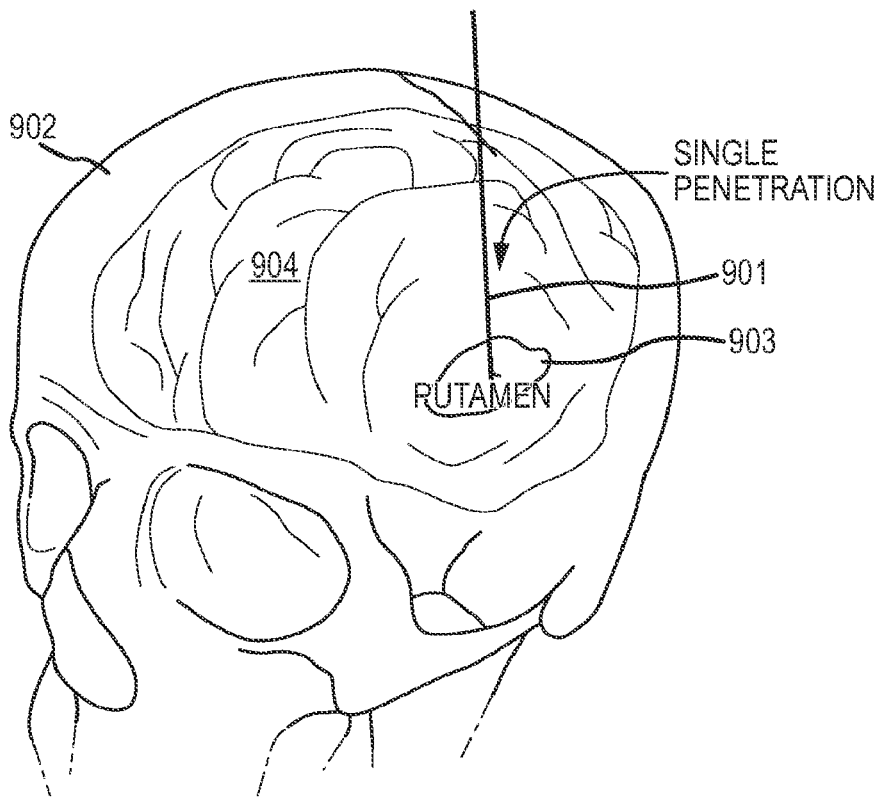
FIG. 9 illustrates the use of a single penetration of a skull to reach the putamen of a brain, in accordance with embodiments.
Figure 10:
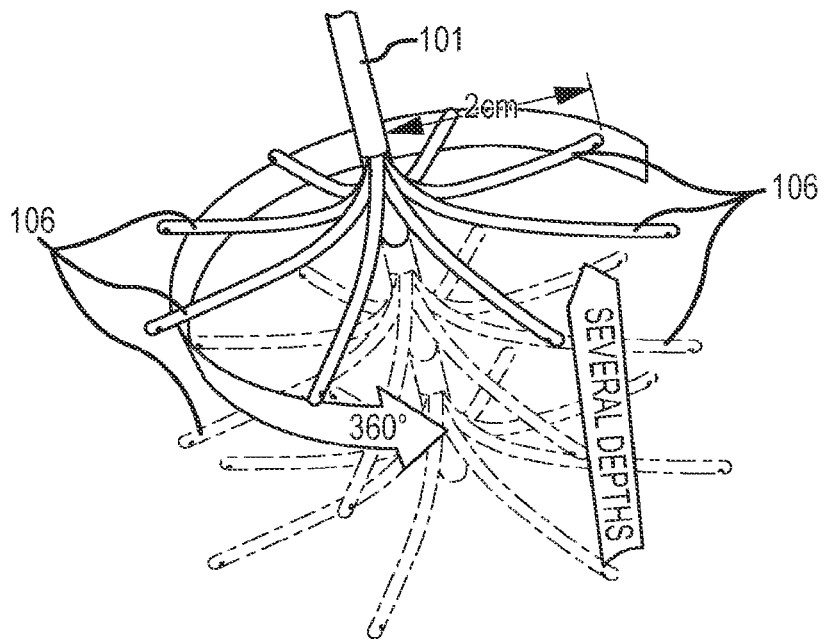
FIG. 10 illustrates a "tree-like" pattern of treatment sites that may be reached through a single penetration into patient tissue, in accordance with embodiments.

FIG. 9 illustrates the use of a single penetration 901 of the skull 902 to reach the putamen 903 of a brain 904. FIG. 10 illustrates a "tree-like" pattern of treatment sites that may be reached through a single penetration of outer guide tube 101 into patient tissue. Catheter 106 may be placed in several different rotational positions and several depths, resulting in a relatively large number of treatment sites accessible through the single penetration. The treatment volume may have a radius or up to 2 cm or more.

Figures 11A, 11B:
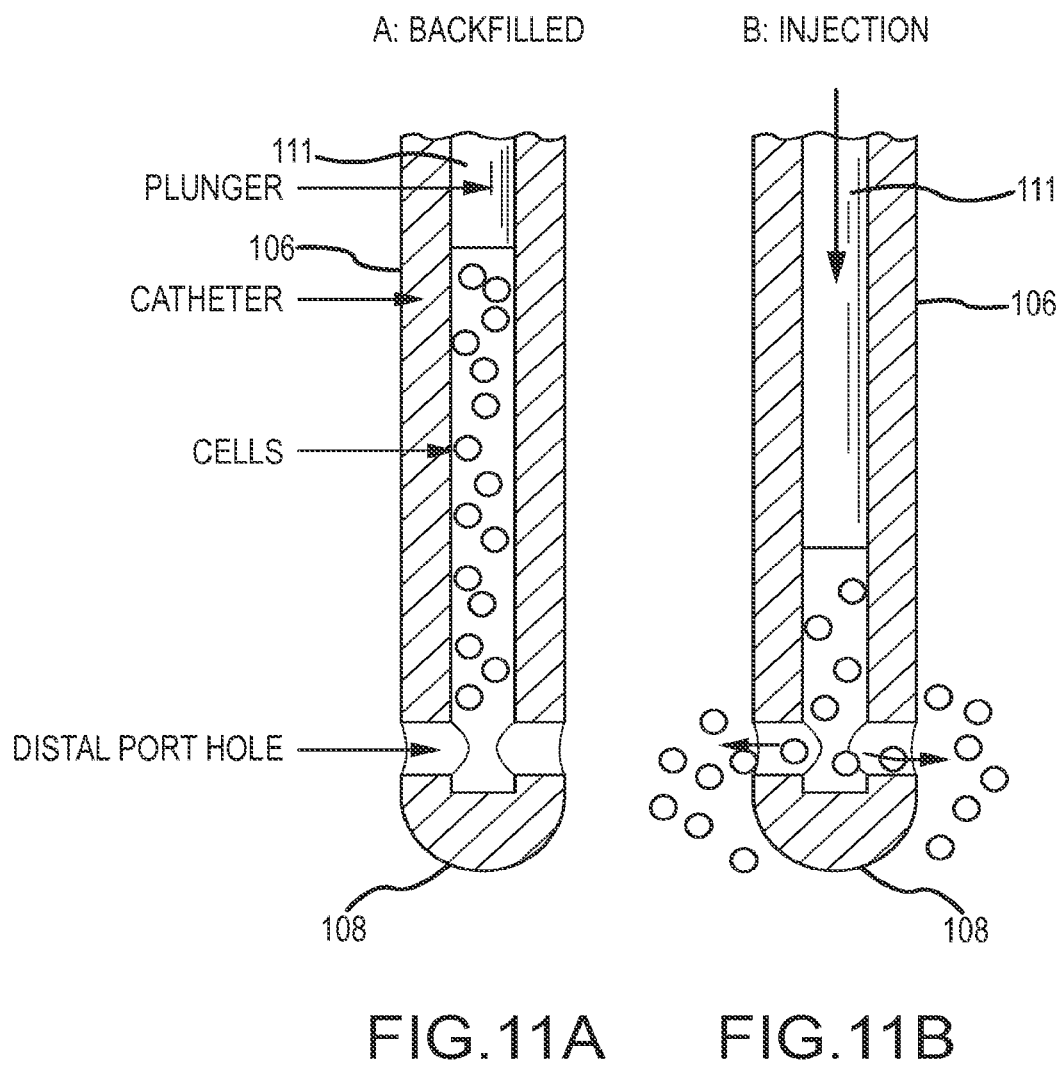
FIGS. 11A and 11B illustrate an example embodiment of reloading a catheter, and dispensing media from the reloaded catheter.

As was mentioned above, a close fit between the walls of catheter 106 and plunger 111 may provide a nearly gas-tight seal to allow aspiration of media 110. Accordingly, one method of loading catheter 106 is to insert plunger 111 into catheter 106, and advance plunger 111 until it has reached closed insertion end 108. This system can then be placed into a media or solution, and plunger 111 withdrawn to any location along the catheters long axis, creating a suction force (negative pressure) that will drive, or load, the media from the one or more dispensing holes 109 into the main lumen of catheter 106. This process is illustrated in FIG. 11A. Once the operator has loaded the appropriate dose, depending on how far plunger 111 has been withdrawn from the long axes of the main lumen of catheter 106, the media 110 can then be placed into the appropriate target location in the patient as previously described and shown in FIG. 11B.

One advantage of an insertion device according to embodiments, as compared with previous systems, may be that reflux of the dispensed media is significantly reduced. In an experimental evaluation, an insertion device embodying the invention was used to inject 10 µl of Allura Red AC dye into an agarose gel that mimics the gross structural characteristics of brain. The catheter was deployed 7 cm below the gel surface, and dye was infused using a plunger advancement rate of 2 µl/min. No dye was observed to reflux up the tract created by the outer guide tube. Reflux was arrested at the transition point between the deployed catheter and the outer guide tube side port. This surprising resistance to reflux may be a consequence of the directional change of the tract and the larger caliber of the outer guide tube. By contrast, delivery of 10 µl of dye through a 20G cannula-syringe system inserted to the same depth resulted in significant reflux of dye. This difference in reflux was also observed when MRI was used to track the delivery of a suspension of paramagnetic beads to an agarose gel contained within a model skull.

An insertion device according to embodiments of the invention may promote cell viability when the device is used to deliver cells to a treatment site. The system has a comparatively short and uniform flow path for cells, so that few opportunities arise for shear forces induced by the flow of media 110 to injure cells in the media. Additionally, the small diameter of plunger 111 enables the precise dispensing of very small quantities of media 110 to a large number of sites. For example, in one experimental embodiment, the volume of media 110 delivered by 1 cm of plunger travel was only 1.36 µl. Thus comparatively few cells compete for the available oxygen at any particular treatment site.

Figure 12:
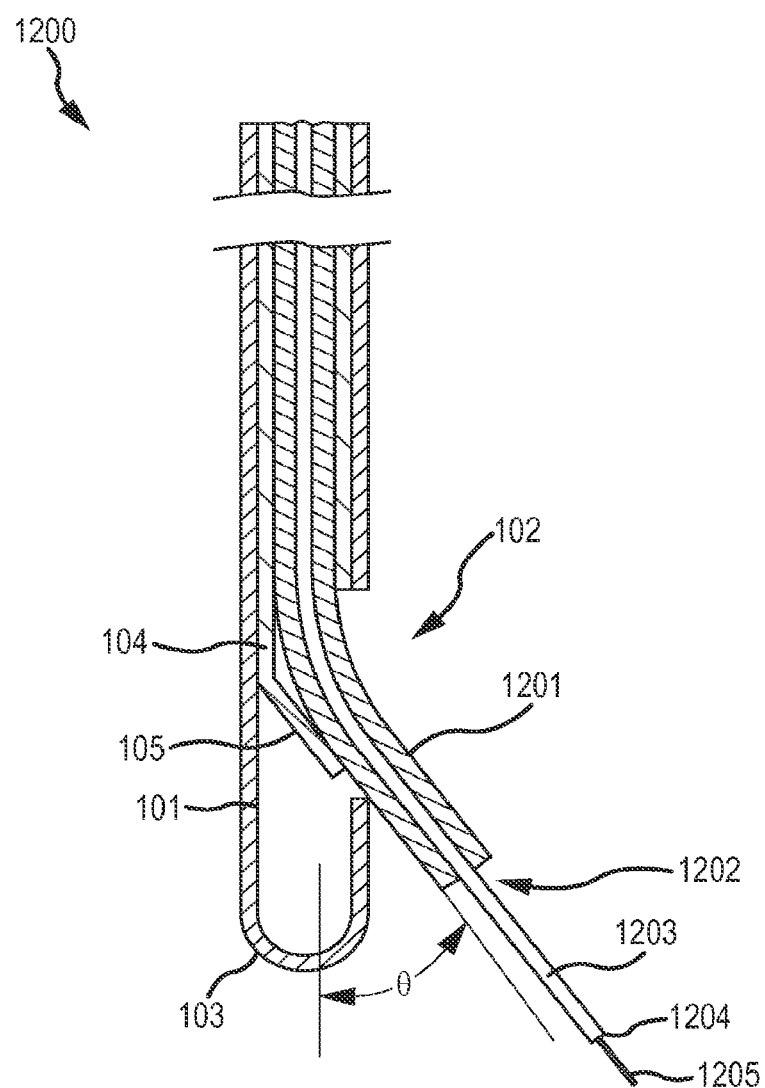
FIG. 12 illustrates an insertion device in accordance with another embodiment of the invention.

FIG. 12 illustrates an insertion device 1200 in accordance with another embodiment of the invention. Insertion device 1200 has several components similar to components of insertion device 100 discussed above, and these components are designated with the same reference numerals. For example, outer guide tube 101 may be rigid or semi-rigid, and may be made for of stainless steel, polyetheretherketone (PEEK), or another suitable material. Outer guide tube 101 includes a side port 102, and a closed distal end 103 for insertion into tissue such as brain tissue. In one example embodiment, outer guide tube has an outer diameter of about 2.0 mm, an inner diameter of about 1.5 m, and a length of about 38 cm, although different sizes may be used for different applications.

Inner guide tube 104 nests within outer guide tube 101. Inner guide tube 104 may also be rigid or semi-rigid, and may be made for example of stainless steel, nylon-12, or another suitable material. In one example embodiment, inner guide tube 104 has an outer diameter of about 1.47 mm, an inner diameter of about 1.07 mm, and a length of about 43 cm or more, although other suitable dimensions may be used. Inner guide tube 104 is movable at least axially within outer guide tube 101, so that inner guide tube can cover or uncover (close or open) side port 102. Inner guide tube 104 may be lockable in the open and closed positions with respect to outer guide tube 101, for example using a Tuohy Borst adapter or other device (not shown). Inner guide tube 104 also includes a deflector 105.

A flexible delivery catheter 1201 translates within inner guide tube 104. Catheter 1201 may be made, for example, of nylon-12, nylon-11, or another suitable material. In one example embodiment, catheter 106 has an outer diameter of about 0.40 mm and an inner diameter of about 0.38 mm, but other suitable dimensions may be used. Catheter 1201 may be lockable with respect to inner guide tube 104, for example using another Tuohy Borst adapter or other device (not shown). A depth stop may be provided to prevent inadvertent deployment of catheter 1201 beyond its intended range. Similar to catheter 106 described above, delivery catheter 1201 preferably is formed into a curved shape near insertion end 1202, using a heat set or other operation.

In contrast to catheter 106, delivery catheter 1201 is open at insertion end 1202, and serves as a conduit for a therapeutic delivery cannula 1203. Therapeutic delivery cannula 1203 may be, for example a step cannula as shown in FIG. 12, having a step 1204 in its diameter near distal end 1205, and suitable for delivering biologics to a brain or other tissue via convection enhanced delivery.

However, it will be recognized that a wide variety of other cannula types and delivery methods may be used. Therapeutic delivery cannula 1203 is preferably made of a semi-rigid material such as Nitinol, and is flexible enough that it can be guided by catheter 1201. However, therapeutic delivery cannula 1203 preferably does not include a pre-formed curved shape, so that therapeutic delivery cannula 1203 tends to maintain a straight configuration unless acted on by another element such as catheter 1201. In one example embodiment, therapeutic delivery cannula is a step cannula made of Nitinol having an outside diameter of 0.375 mm over much of its length, an outside diameter of 0.150 mm below step 1204 at distal end 1205, and an inner diameter of 0.0625 mm.

To use insertion device 1200, the user preferably plans an insertion trajectory into the tissue of the patient. Where feasible, the insertion may be planned and accomplished using stereotactic surgery techniques as described above.

Whatever means are used to guide the insertion, at least outer guide tube 101 and inner guide tube 104 are inserted into the patient tissue to the desired insertion depth. Preferably, inner guide tube 104 is positioned so that side port 102 is closed during the insertion. Once the desired insertion depth is reached, the position of outer guide tube 101 may be locked. Catheter 1201 and therapeutic delivery cannula 1203 may be present within inner guide tube 104 during the insertion or may be inserted later.

Therapeutic delivery cannula 1203 is loaded at any convenient time with media to be dispensed to the patient tissue. Side port 102 is opened by withdrawing inner guide tube 104, and inner guide tube 104 is preferably locked with respect to outer guide tube 101. Catheter 1201 (possibly along with therapeutic delivery cannula 1203) is advanced so that dispensing end 1202 emerges through side port 102. In contrast to the use of delivery device 100 described above, catheter 1201 may be advanced only a relatively small distance from inner guide tube 104. The distance is sufficient to establish a desired delivery angle $\Theta$ of delivery end 1202 with respect to outer guide tube 101, but the distance is small enough to avoid any appreciable "sweep" of catheter 1201 through the tissue. Sweep may occur, for example, when a curved catheter is advanced into tissue and, due to its curvature and stiffness, tends to sweep through the tissue transverse to the longitudinal axis of the catheter, rather than following the longitudinal axis narrowly through the tissue. Because catheter 1201 is advanced only a small distance, it has little or no opportunity to sweep through the tissue.

Once the desired protrusion distance is reached, catheter 1201 is preferably locked in relation to inner guide tube 104. Therapeutic delivery cannula 1203 is then advanced through catheter 1201 to reach the relatively distant treatment site. The curve of catheter 1201 directs therapeutic delivery cannula 1203 in the direction of angle $\Theta$, but once therapeutic delivery cannula 1203 emerges from catheter 1201, catheter 1201 no longer influences the direction of travel of therapeutic delivery cannula 1203. Because therapeutic delivery cannula 1203 is semi-rigid and is straight in its natural condition, it tends to proceed through the tissue along a straight line, without a tendency to sweep. A therapeutic agent may then be delivered through therapeutic delivery cannula 1203 by any suitable means, for example by convection enhanced delivery.

Once the desired dose has been delivered to a first treatment site, the process may be reversed to withdraw therapeutic delivery cannula 1203 and catheter 1201 back into inner guide tube 104, and to close side port 102. Outer guide tube may then be repositioned for delivery of media to a second treatment site. During the repositioning, outer guide tube 101 may be translated along its longitudinal axis (either advanced or retracted), rotated about its longitudinal axis, or moved in a combination of translation and rotation. When outer guide tube 104 is in the desired position for dispensing media to a second treatment site, inner guide tube 104 is retracted to open side port 102, catheter 1201 is advanced, and therapeutic delivery cannula 1203 is advanced to another treatment site where a therapeutic agent is delivered.

Figure 13:
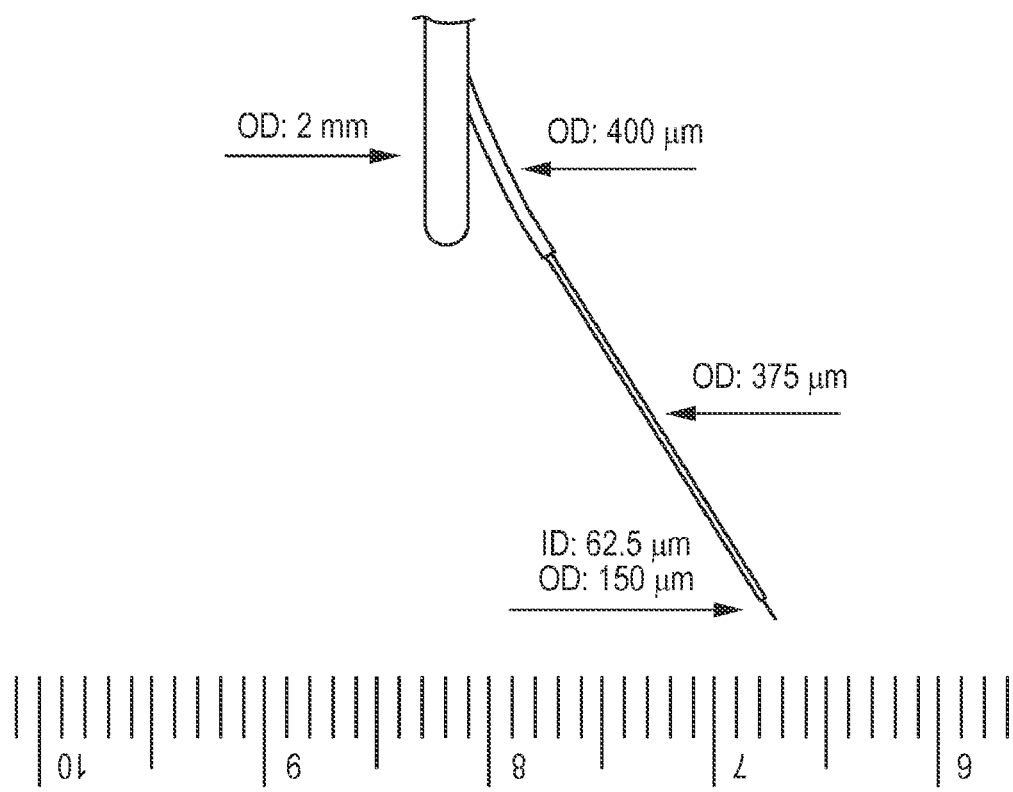
FIG. 13 is a rendering of an actual insertion of a delivery device similar to the delivery device of FIG. 12 into an Agarose gel, simulating insertion into patient tissue.

This process may be repeated, so that a number of different treatment sites are accessed through a single original penetration of outer guide tube 101 into the patient tissue. FIG. 13 is a rendering of an actual insertion of a delivery device similar to insertion device 1200 into an Agarose gel, simulating insertion into patient tissue.

Figure 14:
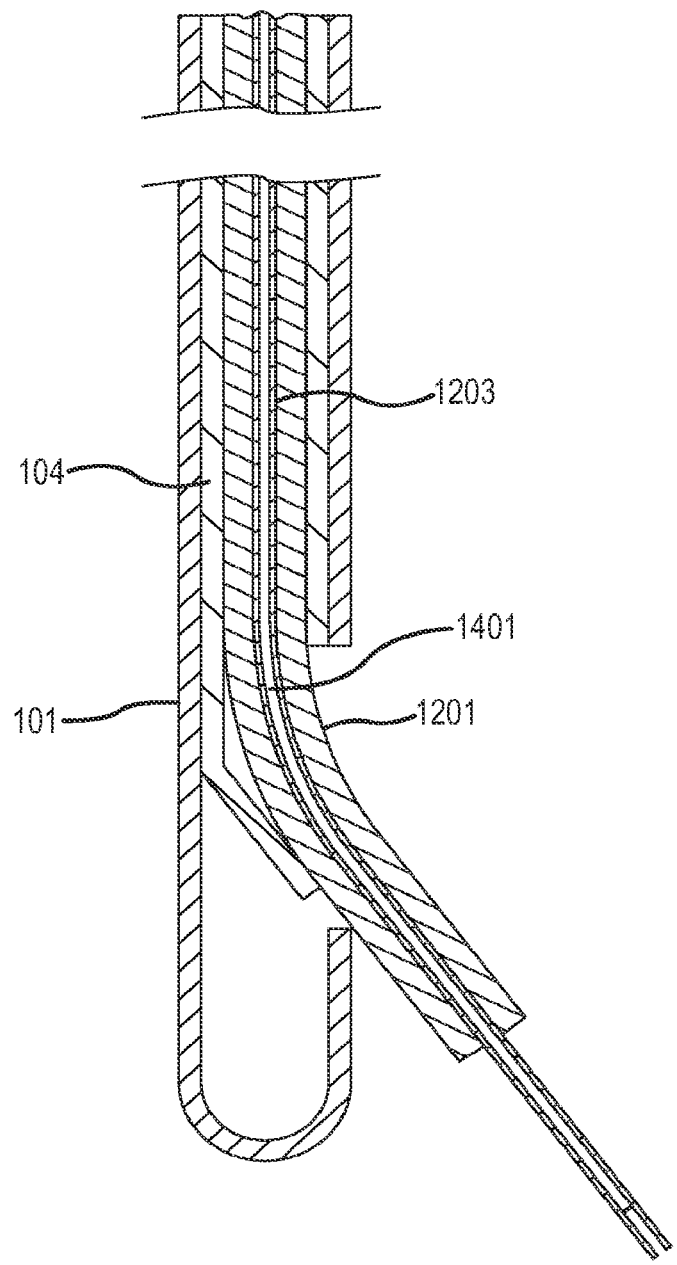
FIG. 14 illustrates a delivery device according to another embodiment of the invention.

While delivery of a therapeutic agent through therapeutic delivery cannula 1203 may be accomplished by any suitable method, in some embodiments a plunger similar to plunger 111 discussed above may be used. FIG. 14 illustrates a delivery device 1400 according to this embodiment. Delivery device 1400 is similar to insertion device 1200 in construction and use, with the addition of plunger 1401 within therapeutic delivery cannula 1203. Thus, delivery device 1400 includes five nested elements: outer guide tube 101, inner guide tube 104, delivery catheter 1201, therapeutic delivery cannula 1203, and finally plunger 1401. As before, the use of plunger 1401 enables very accurate dosing of a therapeutic agent, because the plunger is of a relatively small diameter and moves a relatively large distance during dispensing, allowing very fine control of the amount of agent dispensed.

It will also be recognized that steps in the operation of the delivery device described above may be performed in any suitable order. For example, catheter 1201 may be inserted into inner guide tube 104 and advanced through side port 102 before therapeutic delivery cannula 1203 (and plunger 1401 if present) is inserted into catheter 1201. Alternatively, catheter 1201, therapeutic delivery cannula 1203, and plunger 1401 (if present) could be advanced together to the extent of the advancement of catheter 1201. Catheter 1201 may then be fixed, and therapeutic delivery cannula 1203 and plunger 1401 advanced beyond the insertion end of catheter 1201 to reach the treatment site. Many other sequences are possible.

Therapeutic delivery cannula 1203 may be withdrawn and re-loaded in a manner similar to catheter 106 described above, or in any other suitable manner.

Figure 15:
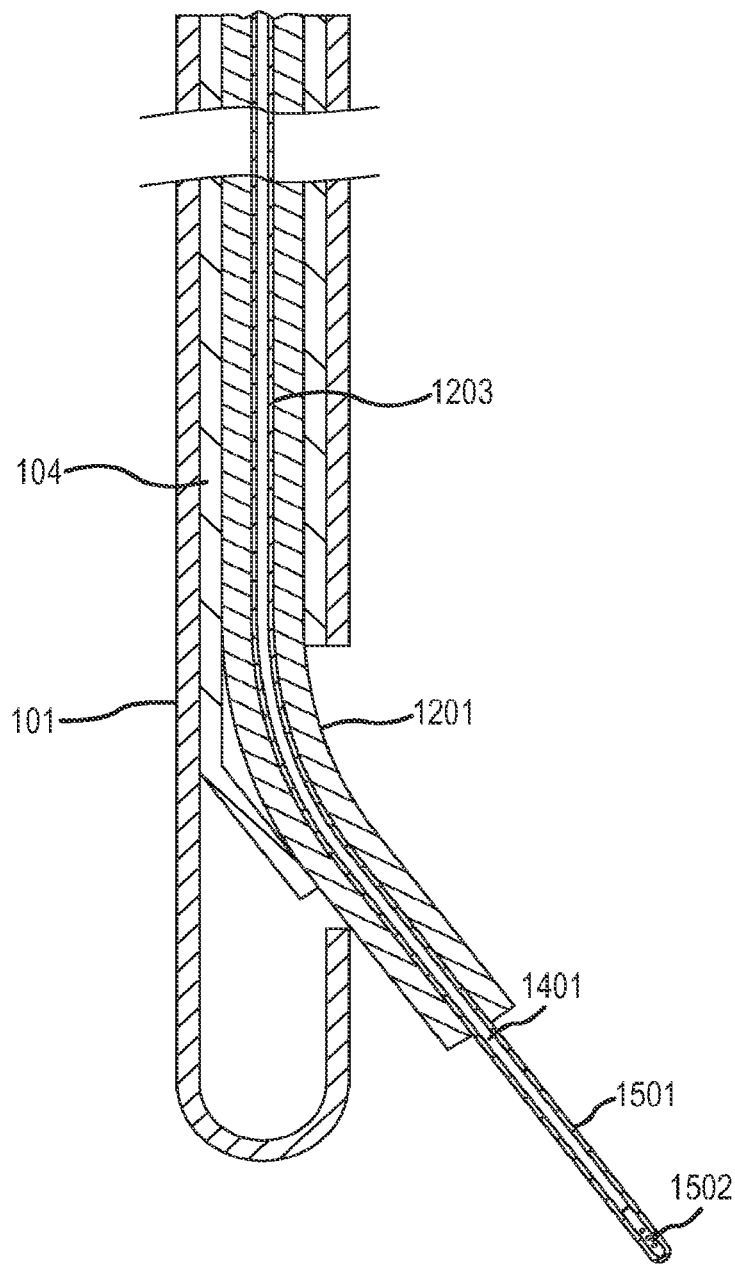
FIG. 15 shows an embodiment in which a therapeutic delivery cannula includes openings.

While therapeutic delivery cannula 1203 is shown as open ended, this is not a requirement. For example, therapeutic delivery cannula could have a closed end similar to catheter 106 discussed above, including side openings similar openings 109. This arrangement may be especially suitable for delivering a suspension of cells for cell therapy as discussed above. FIG. 15 shows such an embodiment, in which therapeutic delivery cannula 1501 includes openings 1502.

In addition to the delivery of therapeutic agents described in the above embodiments, other embodiments may enable delivery of other kinds of therapy. For example, an electric therapeutic such as an electrode may be delivered in place of or through therapeutic delivery cannula 1203.

Embodiments of the invention have now been described in detail for the purposes of clarity and understanding. However, those skilled in the art will appreciate that certain changes and modifications may be practiced within the scope of the appended claims. It is to be understood that all workable combination of the components and features described herein are considered to be disclosed.

What is claimed is:

1. An insertion device for delivering media inside a patient, the insertion device comprising:
    an outer guide tube having a closed end, the outer guide tube defining a side port in a wall of the outer guide tube proximate to the closed end;
    an inner guide tube nested within the outer guide tube and movable axially within the outer guide tube, the inner guide tube comprising a deflector at an end of the inner guide tube within the outer guide tube, the inner guide tube configured to, when in a closed position, cover the side port and further configured to, when in an open position, uncover the side port; and
    a catheter nested within the inner guide tube and movable axially and rotationally within the inner guide tube and including an insertion end,
    wherein when the inner guide tube is disposed in the open position, the deflector extends from a side of the inner guide tube opposite the side port to the side port and is configured to align with the side port of the outer guide tube, and wherein the deflector alignment with the side port deflects the insertion end of the catheter outward through the side port in the outer guide tube when the catheter is advanced axially within the inner guide tube.

2. The insertion device of claim 1, wherein the catheter includes a preset bend at the insertion end.

3. The insertion device of claim 2, further comprising a set of catheters having a variety of preset bends.

4. The insertion device of claim 1, wherein the insertion end of the catheter is a dispensing end defining one or more dispensing holes for dispensing the media.

5. The insertion device of claim 4, further comprising a plunger within the catheter and axially movable within the catheter to force the media out of the catheter through the one or more dispensing holes.

* * * * *